(12) United States Patent
Bazargan et al.

(10) Patent No.: US 8,070,723 B2
(45) Date of Patent: Dec. 6, 2011

(54) ACTIVITY GUARD

(75) Inventors: Afshin Bazargan, Simi Valley, CA (US); Sheldon B. Moberg, Thousand Oaks, CA (US); Kevin Lee Bokelman, San Diego, CA (US); Daniel S. Kline, Encinitas, CA (US); Steven Masterson, Encinitas, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 3 days.

(21) Appl. No.: 12/651,262

(22) Filed: Dec. 31, 2009

(65) Prior Publication Data

US 2011/0160667 A1 Jun. 30, 2011

(51) Int. Cl.
*A61M 5/00* (2006.01)
(52) U.S. Cl. ......................................................... 604/110
(58) Field of Classification Search .................. 604/110, 604/111
See application file for complete search history.

(56) References Cited

U.S. PATENT DOCUMENTS

| | | | | |
|---|---|---|---|---|
| 4,645,494 A * | 2/1987 | Lee et al. | ...................... | 604/175 |
| 4,946,074 A * | 8/1990 | Grogan | .................... | 222/153.13 |
| 5,297,701 A * | 3/1994 | Steijns et al. | ............. | 222/153.05 |
| 5,810,792 A * | 9/1998 | Fangrow et al. | ............... | 604/533 |
| 6,003,738 A * | 12/1999 | Foster et al. | ................... | 222/384 |
| 6,145,688 A * | 11/2000 | Smith | ........................ | 220/259.3 |
| 6,286,723 B1 * | 9/2001 | Sweeton et al. | .......... | 222/153.13 |
| 6,431,468 B1 * | 8/2002 | Brown et al. | .................. | 239/526 |
| 6,474,510 B2 * | 11/2002 | Frutin | ....................... | 222/153.11 |
| 6,488,650 B1 * | 12/2002 | Epstein et al. | ................... | 604/82 |
| 6,817,990 B2 * | 11/2004 | Yap et al. | ....................... | 604/228 |
| 7,326,194 B2 * | 2/2008 | Zinger et al. | ................... | 604/410 |
| 7,354,008 B2 * | 4/2008 | Hester et al. | ............... | 239/589.1 |
| 7,628,782 B2 * | 12/2009 | Adair et al. | ..................... | 604/523 |
| 7,632,263 B2 * | 12/2009 | Denoth et al. | ................ | 604/523 |
| 7,678,079 B2 * | 3/2010 | Shermer et al. | ............... | 604/134 |
| 2009/0099523 A1 * | 4/2009 | Grant et al. | .................... | 604/151 |

\* cited by examiner

*Primary Examiner* — Nicholas D Lucchesi
*Assistant Examiner* — Diva Ranade
(74) *Attorney, Agent, or Firm* — Medtronic MiniMed, Inc.

(57) ABSTRACT

The fluid infusion system is disclosed that includes a pump housing that has a reservoir cavity and is designed to be pocketable. The reservoir cavity has a rim and helical coupling features formed on an interior face of the reservoir cavity. The fluid infusion system further has a reservoir that is removable from the reservoir cavity and the reservoir also has an open end. A removable cap coupled to the pump housing is also included in the fluid infusion system. The cap has corresponding coupling features, an exterior surface and a tab. The corresponding coupling features are defined to couple the cap to the pump housing while the tab is defined as a ridge that extends away from the exterior surface. The tab further has a port to accommodate fluid flow from the reservoir where the port defines an axis of rotation such that torque applied to the tab about the axis of rotation disengages the coupling between the cap and the pump housing. Further included in the infusion system is a guard that is removably coupled to the pump housing. The guard has a slot defined to immobilize rotation of the tab about the axis of rotation.

18 Claims, 7 Drawing Sheets

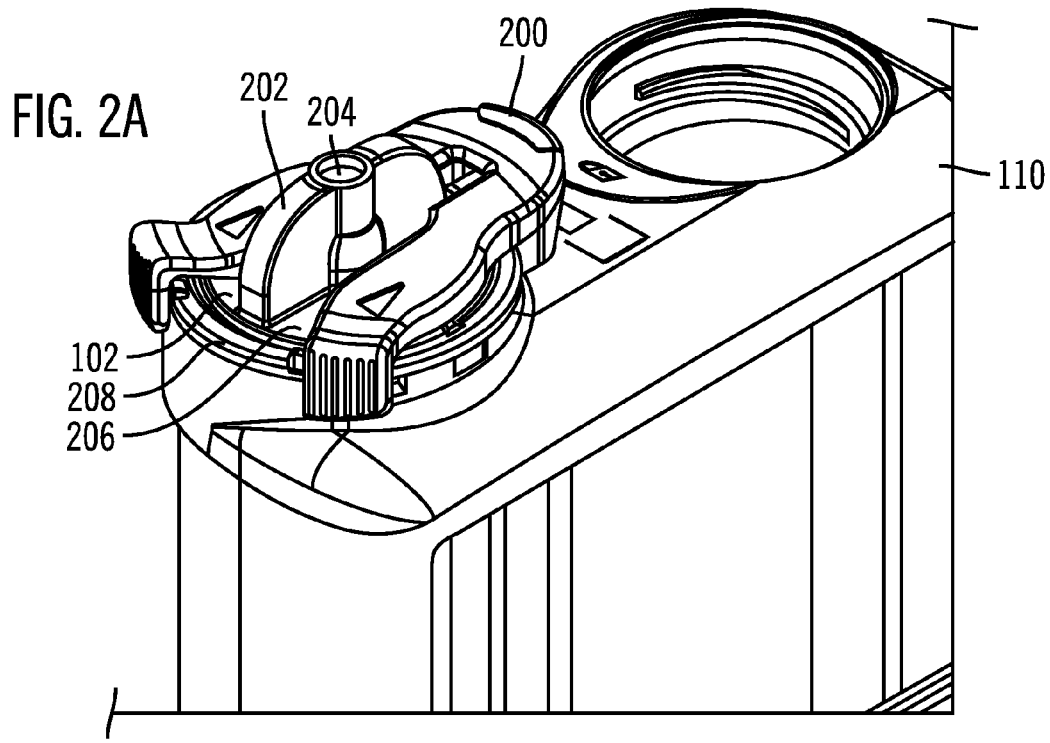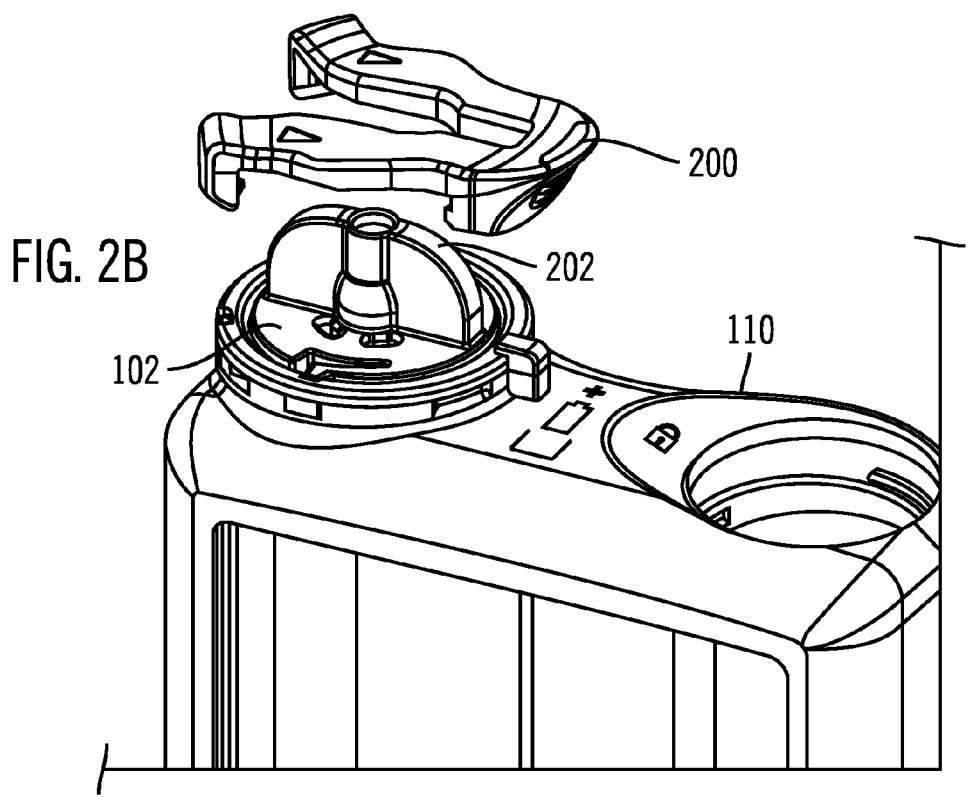

ACTIVITY GUARD

FIELD OF THE INVENTION

Embodiments of the invention relate to diabetes management systems and, more particularly, to securing a fluid reservoir within a portable infusion device.

BACKGROUND OF THE INVENTION

Infusion devices and glucose monitoring systems are relatively well known in the medical arts, particularly for use monitoring blood glucose levels and delivering or dispensing a prescribed medication to a user. In many cases, the user suffers from diabetes—a disease in which the body does not produce or properly use insulin. Approximately 13 million people in the United States have been diagnosed with some form of diabetes. Type 1 diabetes results from the body's failure to produce insulin. Type 2 diabetes results from insulin resistance in which the body fails to properly use insulin. In order to effectively manage and/or control the disease, diabetics must closely monitor and manage their blood glucose levels through exercise, diet and medications in addition to supplying their body with appropriate amounts of insulin based on daily routines. In particular, both Type 1 and Type 2 diabetics rely on insulin delivery and blood glucose monitoring systems to control diabetes.

External infusion devices have been used to deliver medication to a patient as generally described in U.S. Pat. Nos. 4,562,751; 4,678,408; 4,685,903; 6,554,798, and 6,551,276 which are specifically incorporated by reference herein. In recent years, continuous glucose monitoring systems have been developed utilizing the latest sensor technologies incorporating both implantable and external sensors, as generally described in U.S. Pat. No. 5,391,250 entitled "Method of Fabricating Thin Film Sensors", U.S. Pat. No. 6,484,046 entitled "Electrochemical Analyte Sensor," and U.S. Pat. Nos. 5,390,671, 5,568,806 and 5,586,553, entitled "Transcutaneous Sensor Insertion Set," all of which are specifically incorporated by reference herein. Newer systems deliver the preciseness of finger stick measurements coupled with the convenience of not having to repeatedly prick the skin to obtain glucose measurements. These newer systems provide the equivalent of over 200 finger stick readings per day. Additionally, continuous glucose monitoring systems allow physicians and patients to monitor blood glucose trends of their body and suggest and deliver insulin based on each patient's particular needs. Accordingly, physicians and medical device companies are always searching for more convenient ways to keep diabetic patients aware of their blood glucose levels throughout the day.

Diabetic patients utilizing infusion therapy and continuous glucose monitoring systems depend on extremely precise and accurate systems to assure appropriate blood glucose readings and insulin delivery amounts. Furthermore, as younger diabetic patients and diabetic patients with active lifestyles embrace infusion therapy it is imperative to ensure the infusion devices and sensors are robust and reliable.

SUMMARY OF THE DISCLOSURE

In one embodiment a fluid infusion system is disclosed. The fluid infusion system includes a pump housing that has a reservoir cavity and is designed to be pocketable. The reservoir cavity has a rim and helical coupling features formed on an interior face of the reservoir cavity. The fluid infusion system further has a reservoir that is removable from the reservoir cavity and the reservoir also has an open end. A removable cap coupled to the pump housing is also included in the fluid infusion system. The cap has corresponding coupling features, an exterior surface and a tab. The corresponding coupling features are defined to couple the cap to the pump housing while the tab is defined as a ridge that extends away from the exterior surface. The tab further has a port to accommodate fluid flow from the reservoir where the port defines an axis of rotation such that torque applied to the tab about the axis of rotation disengages the coupling between the cap and the pump housing. Further included in the infusion system is a guard that is removably coupled to the pump housing. The guard has a slot defined to immobilize rotation of the tab about the axis of rotation.

In another embodiment a system to retain a fluid medication reservoir within a medication pump housing is disclosed. The system includes a pump housing that is pocketable having a reservoir cavity that has a rim and helical coupling features. The helical coupling features formed on an interior face of the reservoir cavity and having a dimple formed on the rim. The system further includes a reservoir that has an open end and is removable from the reservoir cavity. A cap that is removably coupled to the pump housing is also included in the system. The cap has corresponding coupling features, an exterior surface, and a tab. The corresponding coupling features are defined to couple the cap to the pump housing, and include a snap defined on an edge of the cap that removably interfaces with the dimple on the pump housing. The tab is defined as a ridge that extends away from the exterior surface and the tab has a port to accommodate fluid flow from the reservoir. The port through the tab defines an axis of rotation such that torque applied to the tab about the axis of rotation disengages the coupling between the cap and the pump housing. The system further includes a guard that is removably coupled to the pump housing. The guard has a slot that is defined to immobilize rotation of the tab about the axis of rotation. Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, where like numerals designate corresponding parts or cross-sections in the several figures.

FIGS. 2A and 2B are exemplary perspective views of a portion of the pump housing, with guard installed and removed respectively, in accordance with embodiments of the present invention.

DETAILED DESCRIPTION OF THE PREFERRED EMBODIMENTS

Figure 1:
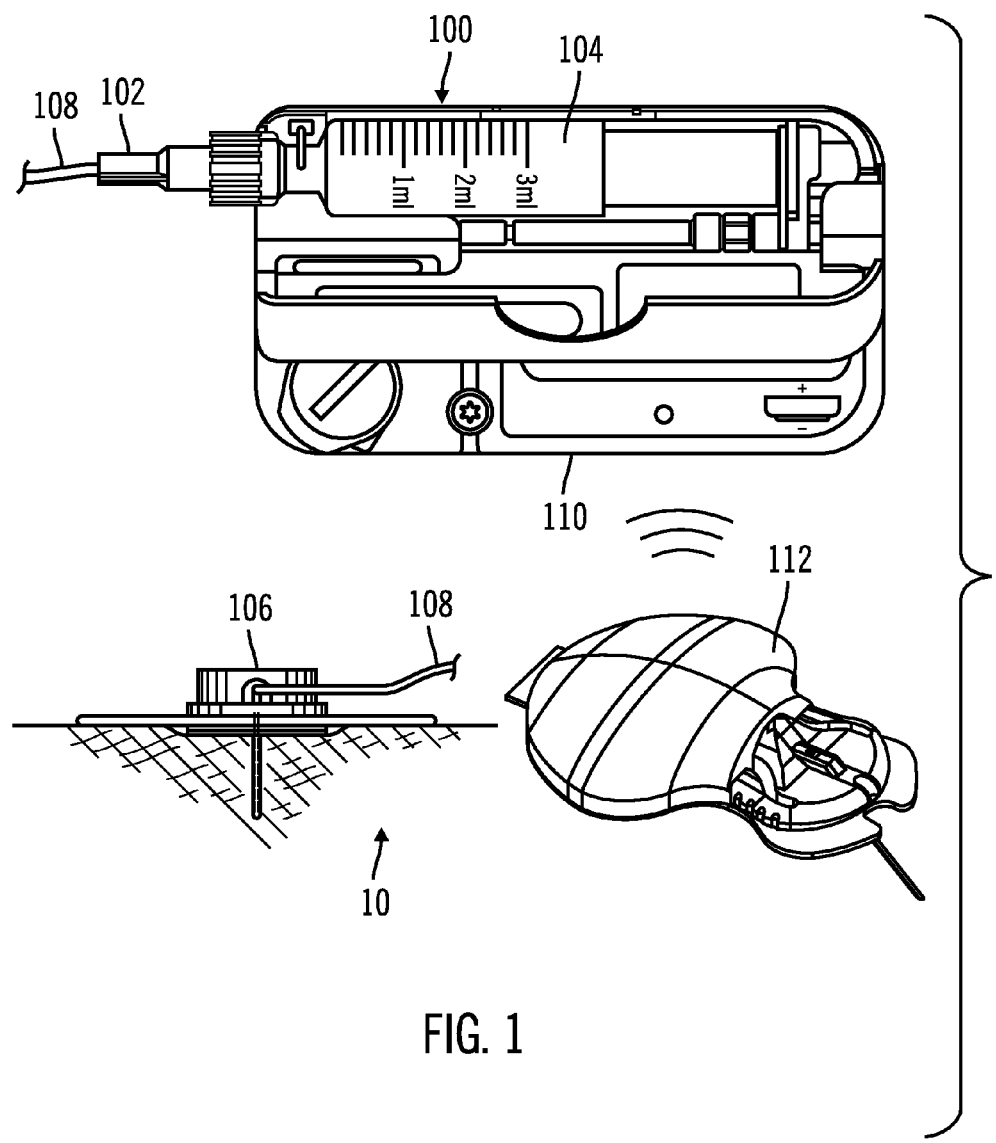
FIG. 1 is an exemplary illustration of a fluid infusion system that includes a pump, an insertion set and a sensor, in accordance with embodiments of the present invention.

FIG. 1 is an exemplary illustration of a fluid infusion system 10 that includes a pump 100, an insertion set 106 and a sensor 112, in accordance with embodiments of the present invention. Mechanical, electrical and software elements of the pump 100 are contained within a pump housing 110. The pump includes a reservoir 104 that is removable from a reservoir cavity within the pump housing 110. The reservoir 104 may be filled with a fluid that can be dispensed from the pump 100 to the insertion set 106 via tubing 108. A cap 102 interfaces with both the pump 100 and the reservoir 104 to connect the tubing 108 with the reservoir 104.

The sensor 112 is an assembly that includes a subcutaneous sensor, a power supply and a radio to transmit data acquired by the sensor to the pump 100. The pump 100 is configured and programmed to be in wireless communication with the sensor 112. For additional information regarding the pump 100 see U.S. Pat. No. 6,554,798 by Mann et al., for additional information regarding the connection between the reservoir 104 and the insertion set 106 see U.S. Pat. No. 6,585,695 by Adair et al., furthermore, for additional information regarding the sensor 112 see U.S. Pat. No. 5,568,806 by Cheney et al., U.S. Pat. No. 6,484,045 by Holker et al., and U.S. Pat. No. 7,003,336 by Holker et al., all of which are incorporated by reference herein. For additional information regarding the use the sensor 112 with a monitor or pump, please see U.S. Pat. No. 6,809,653 by Mann et al. which is incorporated by reference herein.

FIGS. 2A and 2B are exemplary perspective views of a portion of the pump housing 110, with guard 200 installed and removed respectively, in accordance with embodiments of the present invention. The guard 200 interfaces with features on the pump housing 110 and the cap 102. The cap 102 has an exterior surface 206 and a tab 202. In one embodiment the tab 202 is defined as a ridge that extends away from the exterior surface 206. The tab 202 includes a port 204 that can accommodate tubing (not shown). A user can grasp the tab 202 in order to apply a torque to the cap 102 in order to remove the cap 102 and attached reservoir from the pump housing 110. The embodiment illustrated in FIGS. 2A and 2B should not be construed as limiting.

As will be described in more detail in the description of FIG. 3, the pump housing 110 has a rim 208 that includes and enables features that interface with the guard 200. In one embodiment, the rim 208 of the pump housing 110 is formed from a separate part that is mated and permanently affixed to the pump housing 110. Methods of permanently affixing the rim 208 to the pump housing 208 include, but are not limited to the use of insert molding, ultrasonic welding, adhesives or the combination thereof. In other embodiments, the rim 208 and associated features are created during the forming of a one-piece pump housing. Regardless of the whether the rim 208 is formed or installed, the pump housing 110 includes a rim 208 that facilitates the installation and retention of the guard 200.

Figure 2C:
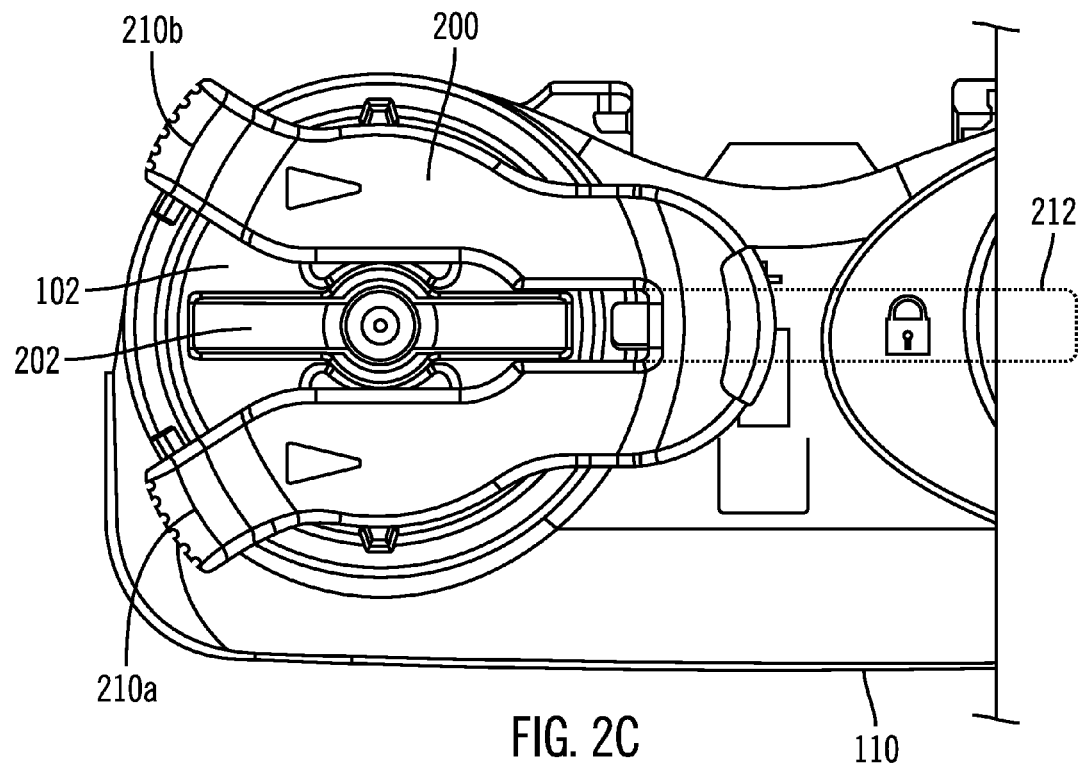
FIG. 2C is a top view illustration of a portion of the pump housing with a guard installed over the cap, in accordance with embodiments of the present invention.

FIG. 2C is a top view illustration of a portion of the pump housing 110 with a guard 200 installed over the cap 102, in accordance with one embodiment of the present invention. As illustrated, the guard 200 includes arms 210a and 210b that are connected. Defined between the arms 210a and 210b is a slot 212. As illustrated, when the cap 102 in installed on the pump housing 110 and a guard 200 in placed over the cap 102, the slot 212 captures the tab 202 to prevent rotation of the tab 202.

Figure 3:
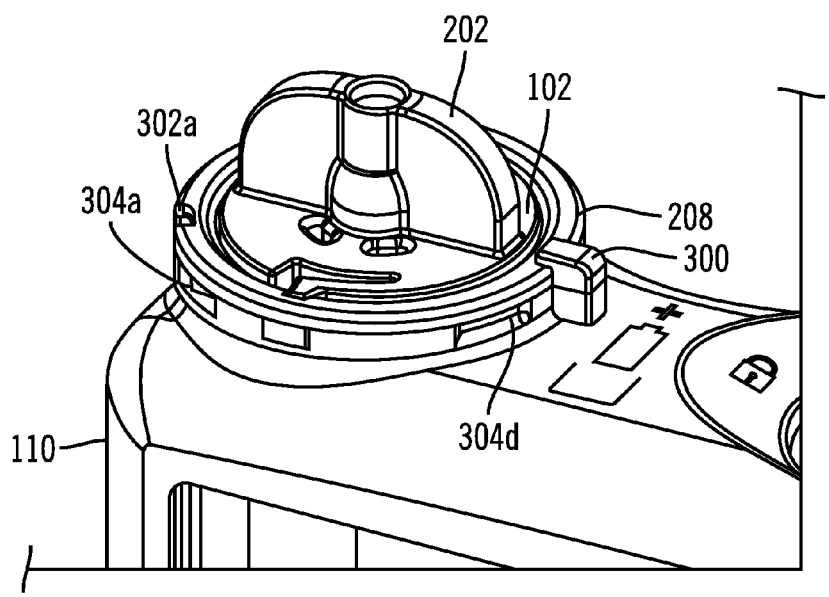
FIG. 3 is a perspective view of the pump illustrating features on the pump housing that are engaged by the guard, in accordance with embodiments of the present invention.

FIG. 3 is a perspective view of the pump 100 illustrating features on the pump housing 110 that are engaged by the guard (not shown), in accordance with embodiments of the present invention. As illustrated, features on the pump housing 110 that are engaged by the guard include, but are not limited to, a rib 300, a nub 302a, and detents 304a and 304d. In one embodiment the nub 302a is formed entirely on the rim 208. Conversely, the rib 300 can be formed when the rim 208 is permanently affixed to the case housing 110. Likewise, detents 304a and 304d can also be formed when the rim 208 is affixed to the pump housing 110. Additional features on the pump housing 110 will be discussed below when the various views of the pump housing 110 reveal the different features.

Figure 4A:
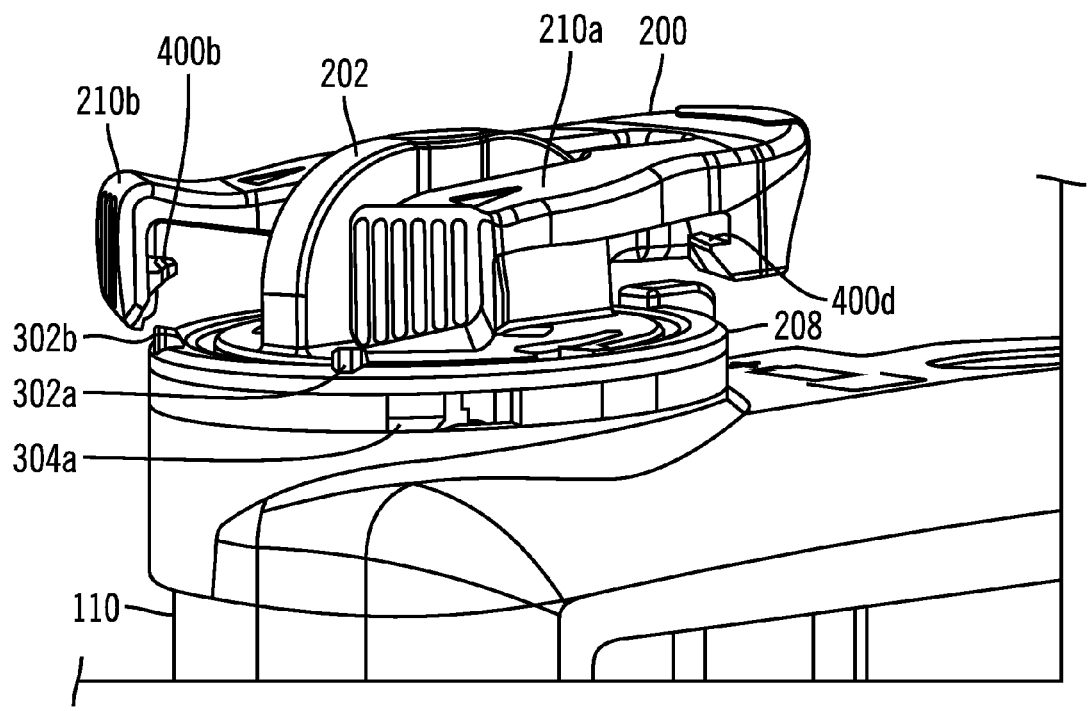
FIGS. 4A and 4B are close-up perspective views illustrating features of the pump housing and the guard, in accordance with embodiments of the present invention.
Figure 4B:
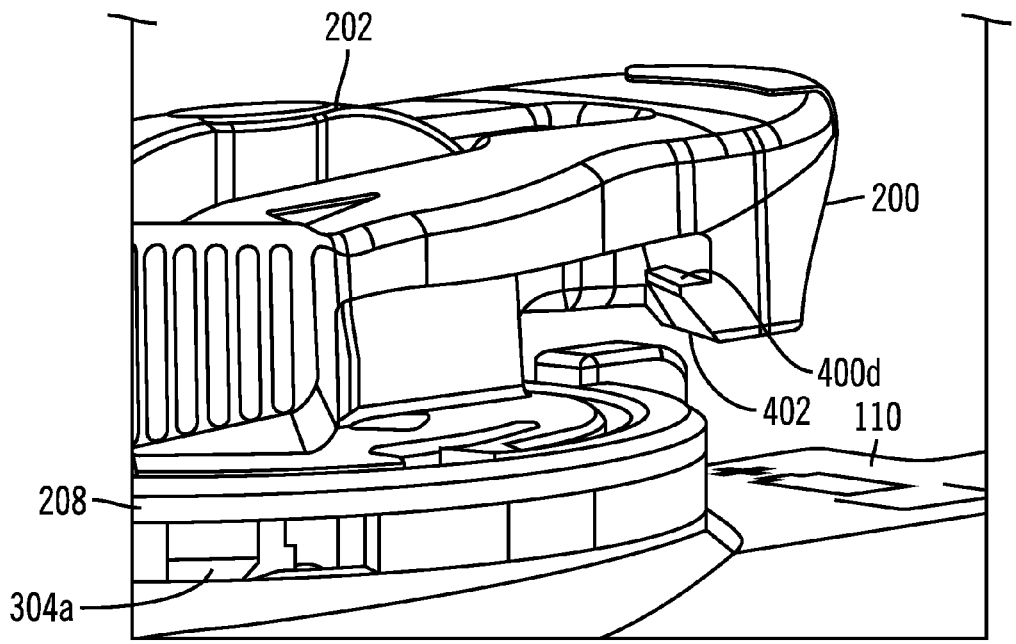

FIGS. 4A and 4B are close-up perspective views illustrating features of the pump housing 110 and the guard 200, in accordance with embodiments of the present invention. Arms 210a and 210b terminate away from the joint with snaps 400a (not shown) and 400b respectively. Each snap 400a and 400b have a corresponding detent 304a and 304b (not shown) formed on the case housing 110. Additionally, snap 400d is formed on arm 210a near the joint between arms 210a and 210b. Similarly, though not shown in FIGS. 4A and 4B, snap 400c is formed on arm 210b. As previously discussed, the detents 304a and 304b can be formed during the fabrication of the case housing 110 or when the rim 208 is affixed to the case housing. In the exemplary embodiment shown in FIG. 4B the snap 400d has a tapered face 402. While not shown, a corresponding snap 400c located on arm 210b can also include a tapered face. The use of the tapered face 402 facilitates the installation of the guard 200 onto the case housing 110. Specifically, the tapered face 402 enables the use of a lower amount of force necessary to pass snap 400d over the rim 208 in order to engage an corresponding detent.

Figure 5A:
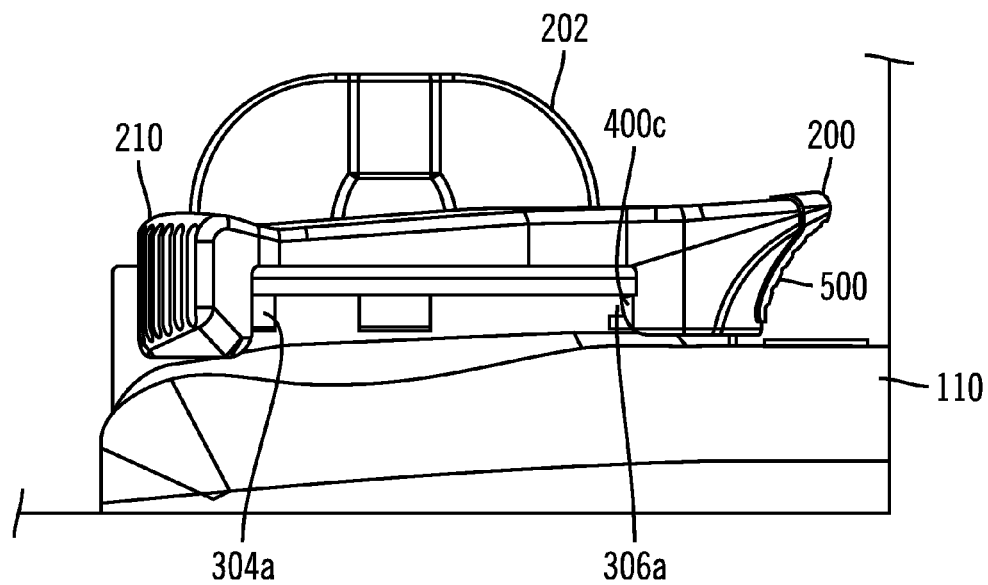
FIGS. 5A-5D are additional views of the pump housing and the guard, in accordance with embodiments of the present invention.

FIGS. 5A-5D are additional views of the pump housing 110 and the guard 200, in accordance with embodiments of the present invention. FIG. 5A is a profile view of the arm 210a and illustrates how detent 304a is engaged by a snap on the terminated arm 210a Likewise, snap 400c is shown engaged in detent 306a. Also visible in FIG. 5A is the profile contour of face 500. The contour of face 500 in conjunction with the placement of snaps 400c enables the repeated removal of guard 200 from the pump housing 110. The face 500 allows user to apply an upward force that can disengage snap 400c and 400d (not shown) from detent 306a and 306b (not shown).

Figure 5B:
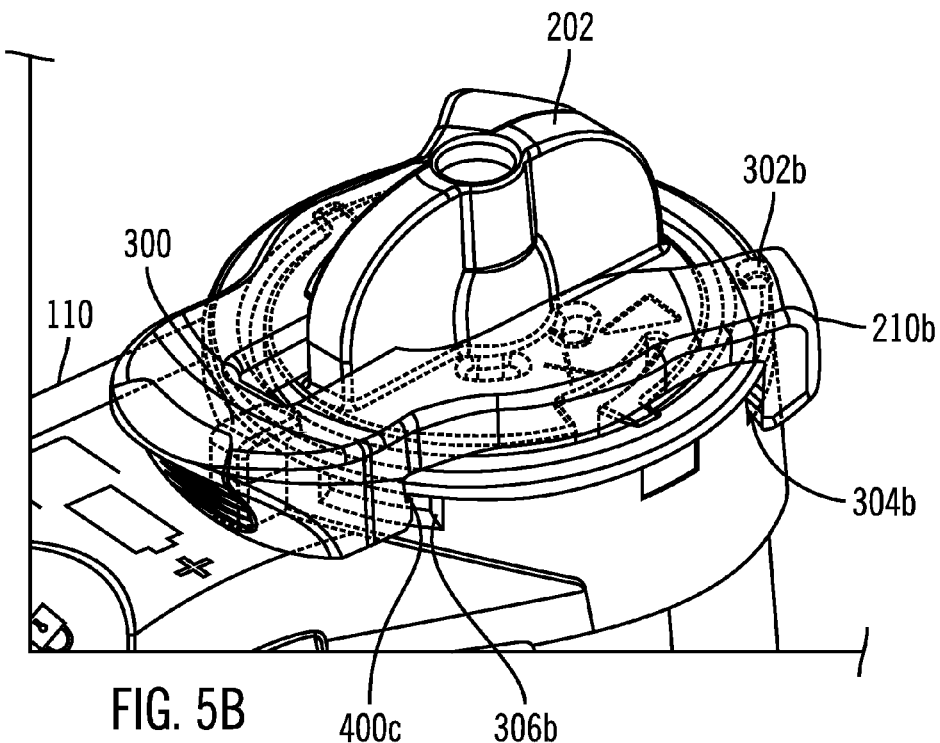
Figure 5C:
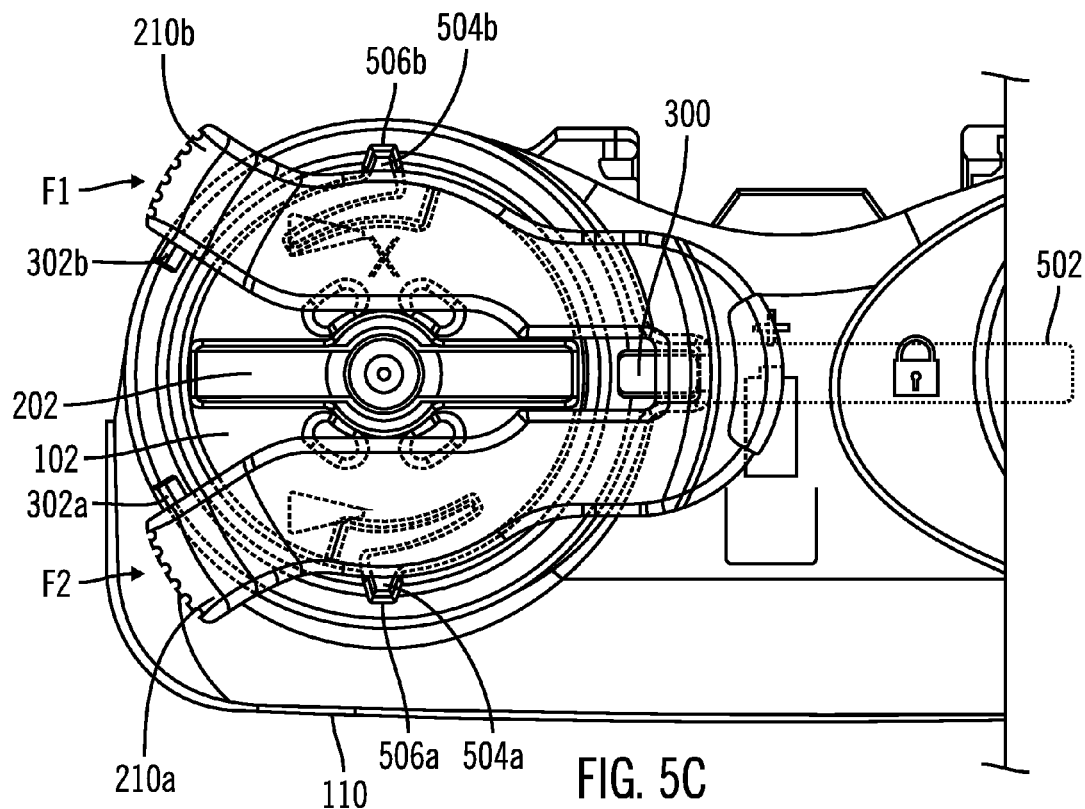

FIGS. 5B and 5C are exemplary illustrations where the guard 200 has been made translucent in order to show how the guard 200 interfaces with the pump housing 110, in accordance with embodiments of the present invention. As FIG. 5B illustrates the arm 210b side of the pump housing 110, snap 400c and detent 306b are visible. FIGS. 5B and 5C also illustrate how the guard 200 includes a recess 502 that interfaces with the rib 300 of the pump housing 110. The recess 502 and the rib 300 work in conjunction with the slot 212 (FIG. 2C) to allow the guard to resist torque applied to the tab 202. The use of both the slot and the rib 300 to prevent rotation of the tab 202 is merely one embodiment. In other embodiments only the slot formed between arms 210a and 210b may be used to counteract rotation of the tab. Similarly, in another embodiment, only the rib 300 and recess 502 may be used to lock the tab 202 by preventing rotation Likewise, additional features can be used to immobilize rotation of the tab in furtherance of either the slot and the rib.

Figure 5D:
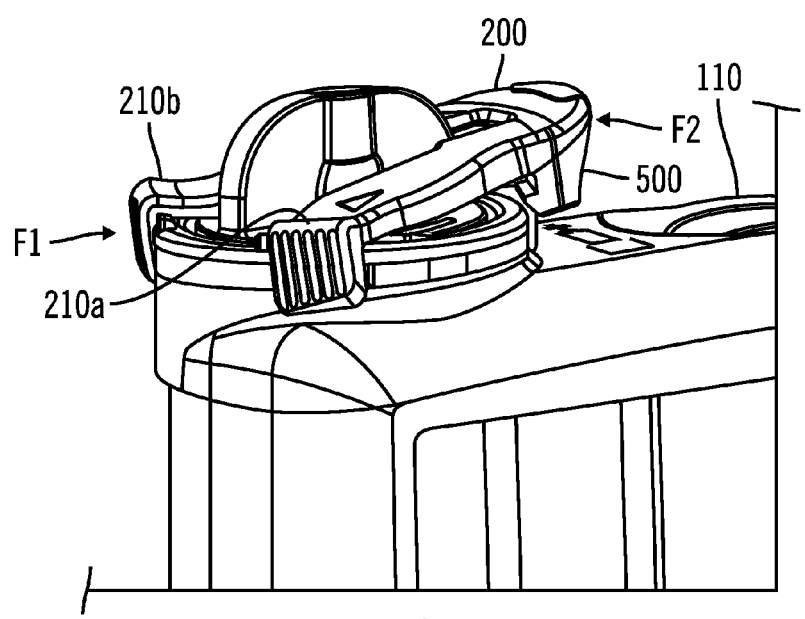

FIGS. 5C and 5D provide an exemplary illustration of the removal of the guard 200 from the pump housing 110, in accordance with embodiments of the present invention. In one embodiment to avoid inadvertent removal, the guard 200 is securely attached to the pump housing 110 and requires two steps to remove the guard 200. To initiate removal of the guard 200, a force $F_1$ is applied to both arms 210a and 210b, as illustrated in FIGS. 5C and 5D. Application of force $F_1$ causes the arms 210a and 210 be spread. Force $F_1$ further pushes the guard 200 toward the rib 300. FIG. 5D illustrates the second step to remove the guard 200, the application of force $F_2$ on face 500 (FIG. 5A). The application of force $F_1$ can help disengage snap 400c (FIG. 5B) and snap 400d (FIG. 4A) thus allowing force $F_2$ to remove the guard 200 from the pump housing 110. As the guard 200 can be installed to prevent children from accidentally removing the cap 102, a two step method (the application of $F_1$ and $F_2$) can make it more difficult for children to remove the guard 200. If $F_2$ is not applied after application of $F_1$ the geometry of the legs is such that the Guard reseats itself.

While it may be beneficial in some instances to have a two step removal process, it should not be construed as required. In other embodiments, a one step removal process may be used while in other embodiments three or more steps may be desired to ensure the guard is difficult to remove. Additionally, for two step removal, the steps outline above should not be considered restrictive as other embodiments of the guard 200 may use a different combination of forces other than $F_1$ and $F_2$.

FIG. 5C further provides an illustration of additional retention features on both the pump housing 110 and the cap 102, in accordance with embodiments of the present invention. The cap 200 includes snaps 504a and 504b that are formed on an outer edge of the cap 200. Included on an interior face of the rim 208 are dimples 506a and 506b that correspond to the snaps 504a and 504b. While FIG. 5C illustrates the use of two snaps 504a and 504b, other embodiments can use fewer or more snaps. Furthermore, while the snaps 504a and 504b are illustrated substantially opposite of each other, other configurations could be used to incorporate fewer or greater number of snaps. For example, snap configurations could include, but are not limited to three equally spaced snaps, four equally spaced snaps, and even a single snap. Still other snap configuration could include snaps that are not equally spaced. In embodiments were the cap 102 utilizes fewer or more snaps that illustrated in FIG. 5C, the rim would have a corresponding number of dimples to accommodate the snaps on the cap.

Figure 6A:
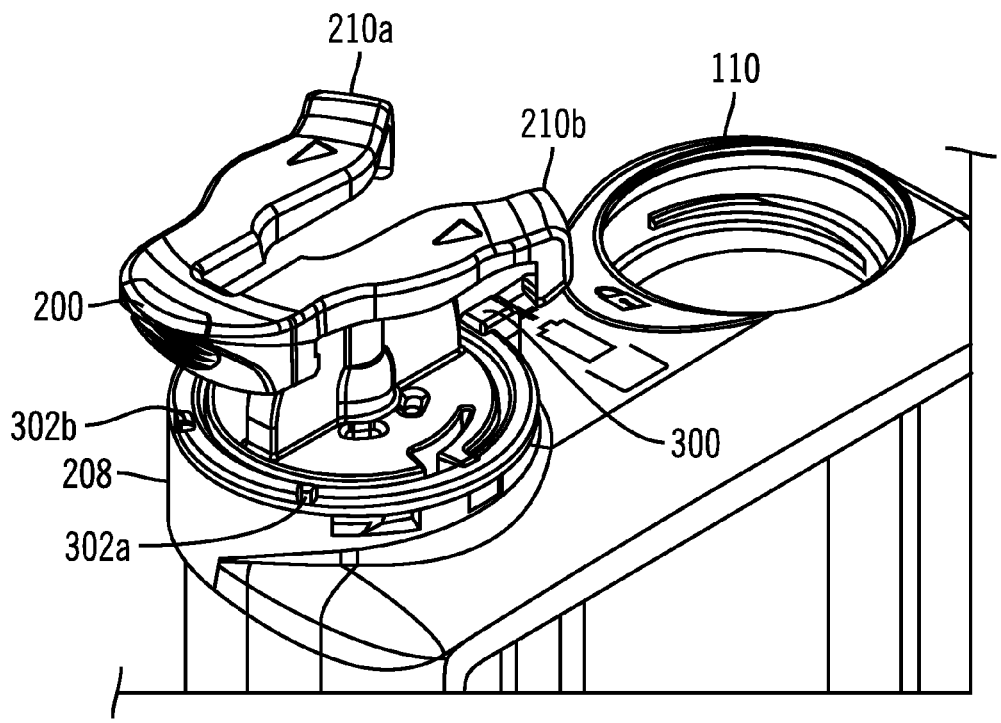
FIGS. 6A and 6B are exemplary perspective illustration showing features that prevent the guard from being installed onto the pump in a reverse orientation, in accordance with embodiments of the present invention.
Figure 6B:
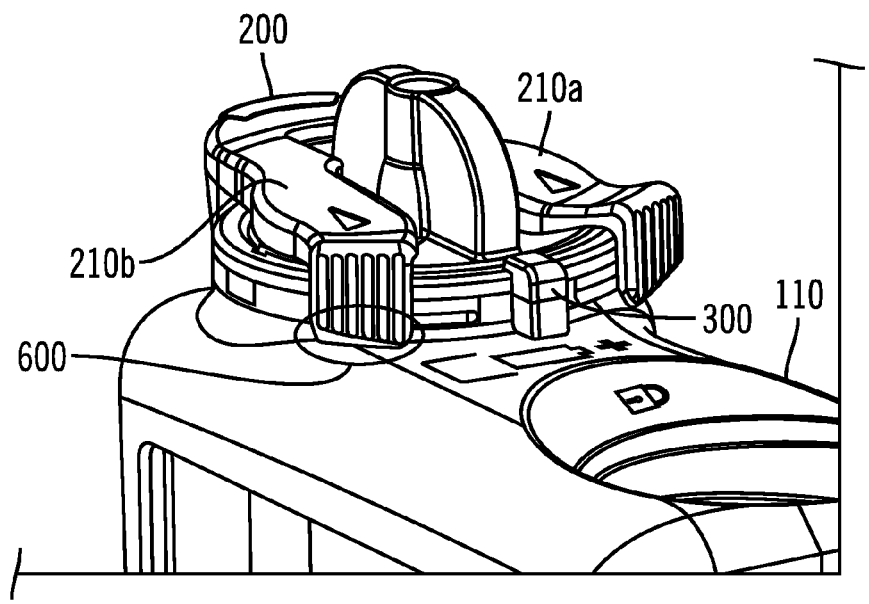

FIGS. 6A and 6B are exemplary perspective illustration showing features that prevent the guard 200 from being installed onto the pump 100 in a reverse orientation, in accordance with embodiments of the present invention. In FIG. 6A the guard 200 is shown in a reverse orientation such that the rib 300 is not aligned with the recess 502 (FIG. 5C) of the guard 200. Nubs 302a and 302b are included on the rim 208 to prevent installation of the guard 200 in this orientation. The nubs 302a and 302b are designed to interfere with the guard 200 and prevent the guard 200 from snapping onto the pump housing 110. In other embodiments, the nubs 302a and 302b are replaced with a rib that extends the surface of the rim 208 to a height equivalent to the nubs 302a and 302b. FIG. 6B is an exemplary illustration showing how the termination of arms 210a and 210b create an interference 600 with the pump housing 110 in order to prevent the guard 200 from being installed in the reverse orientation.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A fluid infusion system comprising:
    a pump housing having a reservoir cavity, the reservoir cavity having a rim and coupling features, the coupling features formed on an interior face of the reservoir cavity, the pump housing further being sized to be pocketable;
    a reservoir being removable from the reservoir cavity, the reservoir having an open end;
    a cap being removably coupled to the pump housing, the cap having corresponding coupling features, an exterior surface and a tab, the corresponding coupling features defined to couple the cap to the pump housing, the tab defined as a ridge that extends away from the exterior surface, the tab further having a port to accommodate fluid flow from the reservoir, the port defining an axis of rotation such that torque applied to the tab about the axis of rotation disengages the coupling between the cap and the pump housing, and
    a guard being removably coupled to the pump housing, the guard having a slot defined between two arms joined at a flexible hinge, the slot defined to immobilize rotation of the tab about the axis of rotation, the two arms each having a snap disposed on an end opposite the flexible hinge.

2. A fluid infusion system according to claim 1, wherein the pump housing includes two detents being formed beneath the rim, the two detents corresponding to the snaps disposed on the arms.

3. A fluid infusion system according to claim 1, wherein the pump housing includes a plurality of detents, the plurality of detents being formed beneath the rim.

4. A fluid infusion system according to claim 3, wherein the guard includes a corresponding plurality of snaps, the corresponding plurality of snaps defined to mate with the plurality of detents.

5. A fluid infusion system according to claim 1, wherein the pump housing includes a first exterior rib, the first exterior rib defined to extend in a direction normal to the rim.

6. A fluid infusion system according to claim 5, wherein the guard includes a recess to capture the first exterior rib of the pump housing.

7. A fluid infusion system according to claim 5, wherein the pump housing includes a second exterior rib, the second exterior rib defined to extend in a direction that is normal from the rim.

8. A fluid infusion system according to claim 7, wherein the second exterior rib prevents the guard from being installed in a reverse orientation.

9. A fluid infusion system according to claim 1, wherein the arms are defined to prevent installation of the guard on the pump housing in a reverse orientation.

10. A system to retain a fluid medication reservoir to a medication pump housing, comprising:
    a pump housing having a reservoir cavity, the reservoir cavity having a rim and coupling features, the helical coupling features formed on an interior face of the reservoir cavity, the coupling features further having a dimple formed on the rim, the pump housing further being sized to be pocketable;

a reservoir being removable from the reservoir cavity, the reservoir having an open end;

a cap being removably coupled to the pump housing, the cap having corresponding coupling features, an exterior surface, and a tab, the corresponding coupling features defined to couple the cap to the pump housing, the corresponding coupling features including a snap defined on an edge of the cap that removably interfaces with the dimple on the pump housing, the tab defined as a ridge that extends away from the exterior surface, the tab further having a port to accommodate fluid flow from the reservoir, the port defining an axis of rotation such that torque applied to the tab about the axis of rotation disengages the coupling between the cap and the pump housing, and a guard being removably coupled to the pump housing, the guard having a slot defined between two arms joined at a flexible hinge, the slot defined to immobilize rotation of the tab about the axis of rotation, the two arms each having a snap disposed on an end opposite the flexible hinge.

11. A system according to claim 10, wherein the medication pump housing includes two detents being formed beneath a rim, the rim on the opening in the medication pump housing, the two detents corresponding to the snaps disposed on the arms.

12. A system according to claim 11, wherein the medication pump housing includes a plurality of detents, the plurality of detents being formed beneath the rim.

13. A system according to claim 12, wherein the guard includes
a corresponding plurality of snaps, the corresponding plurality of snaps defined to mate with the plurality of detents.

14. A system according to claim 10, wherein the medication pump housing includes a first exterior rib, the first exterior rib defined to extend perpendicular from the rim.

15. A system according to claim 14, wherein the guard includes a recess to capture the first exterior rib of the pump housing.

16. A system according to claim 14, wherein the pump housing includes a second exterior rib, the second exterior rib defined to extend in a direction that is normal from the rim.

17. A system according to claim 16, wherein the second exterior rib prevents the guard from being installed in a reverse orientation.

18. A fluid infusion system according to claim 10, wherein the arms are defined to prevent installation of the guard on the pump housing in a reverse orientation.

* * * * *